US010195412B2

(12) United States Patent
Panian (10) Patent No.: US 10,195,412 B2
(45) Date of Patent: Feb. 5, 2019

(54) CAPPING DEVICE FOR A MEDICAL ACCESS CONNECTOR (71) Applicant: CareFusion 303, Inc., San Diego, CA (US)

(72) Inventor: Tyler Devin Panian, Long Beach, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 15/476,805

(22) Filed: Mar. 31, 2017

(65) Prior Publication Data
US 2017/0203088 A1    Jul. 20, 2017

Related U.S. Application Data (63) Continuation of application No. 13/673,981, filed on Nov. 9, 2012, now Pat. No. 9,629,977.

(51) Int. Cl.
A61M 39/10    (2006.01)
A61M 25/00    (2006.01)
A61M 39/20    (2006.01)

(52) U.S. Cl.
CPC ........ *A61M 39/10* (2013.01); *A61M 25/0009* (2013.01); *A61M 39/1011* (2013.01); *A61M 39/1055* (2013.01); *A61M 39/20* (2013.01); A61M 2039/1033 (2013.01); A61M 2039/1038 (2013.01); A61M 2039/1083 (2013.01); A61M 2039/1088 (2013.01)

(58) Field of Classification Search
CPC .............. A61M 39/10; A61M 39/1055; A61M 39/1011; A61M 2039/1038; A61M 2039/1033; A61M 2039/1088; A61M 2039/1083
See application file for complete search history.

(56) References Cited

U.S. PATENT DOCUMENTS

| 3,310,048 | A | 3/1967 | Ewing |
| 4,963,132 | A | 10/1990 | Gibson |
| 4,991,629 | A | 2/1991 | Ernesto et al. |
| 5,078,693 | A | 1/1992 | Shine |

(Continued)

FOREIGN PATENT DOCUMENTS

| CN | 202198946 U | 4/2012 |
| CN | 102458342 A | 5/2012 |

(Continued)

OTHER PUBLICATIONS

Australian Examination Report No. 2 for Application No. 2013341544, dated Oct. 12, 2017, 5 pages.

(Continued)

*Primary Examiner* — Amber Stiles
(74) *Attorney, Agent, or Firm* — Morgan, Lewis & Bockius LLP (57) ABSTRACT A capping device that includes a cap, a first member, a second member, and a living hinge is provided. The cap is for covering the top of a medical access connector. The first member is connected with the cap. The living hinge is located between the first member and the second member. Capping and uncapping the medical access connector with the cap is transparent to a user that is manipulating the medical access connector.

14 Claims, 9 Drawing Sheets (56) References Cited

U.S. PATENT DOCUMENTS

| | | | | |
|---|---|---|---|---|
| 5,385,372 A * | 1/1995 | Utterberg | ............... | A61M 39/20 215/306 |
| 6,231,539 B1 | 5/2001 | Inoue et al. | | |
| 7,922,701 B2 | 4/2011 | Buchman | | |
| 2010/0292673 A1 | 11/2010 | Korogi et al. | | |
| 2011/0139276 A1 | 6/2011 | Kashmiran et al. | | |
| 2012/0016318 A1 * | 1/2012 | Hoang | ................. | A61M 39/16 604/288.01 |

FOREIGN PATENT DOCUMENTS

| | | | |
|---|---|---|---|
| EP | 0460821 A1 | 12/1991 | |
| EP | 0621053 A1 | 10/1994 | |
| JP | H03009165 A | 1/1991 | |
| JP | H04099950 U | 8/1992 | |
| JP | H07047137 A | 2/1995 | |
| JP | 2001095917 A | 4/2001 | |
| JP | 2009529629 A | 8/2009 | |
| WO | WO-2007103998 A2 | 9/2007 | |

OTHER PUBLICATIONS

Chinese Office Action for Application No. 201380064276.X, dated Aug. 21, 2017, 14 pages excluding translation.

Japanese Office Action for Application No. 2015-541826, dated Aug. 8, 2017, 3 pages excluding translation.

Chinese Office Action for Application No. 201380064276.X, dated Dec. 20, 2016, 12 pages excluding translation.

Merriam-Webster Dictionary definition for flush, available online as of Apr. 6, 2016 at http://www.merriam-webster.com/dictionary/flushl.

Merriam-Webster Dictionary definition for integral, defintion Ic, available online as of Apr. 6, 2016 at http://www.merriam-webster.com/dictionary/integral.

International Search Report and Written Opinion for Application No. PCT/US2013/068154, dated Jan. 21, 2014, 8 pages.

Australian Examination Report No. 1 for Application No. 2013341544, dated Jun. 19, 2017, 3 pages.

European Office Action for Application No. 13792169.8, dated Jul. 18, 2017, 5 pages.

Chinese Office Action for Application No. 201380064276.X, dated Feb. 11, 2018, 8 pages excluding English translation.

Japanese Office Action for Application No. 2015-541826, dated Feb. 15, 2018, 2 pages excluding English translation.

Chinese Office Action for Application No. 201380064276.X, dated Aug. 13, 2018, 7 pages.

\* cited by examiner

CAPPING DEVICE FOR A MEDICAL ACCESS CONNECTOR

CROSS-REFERENCE TO RELATED APPLICATION

This Application is a continuation of U.S. Pat. No. 9,629,977, filed Nov. 9, 2012, entitled "CAPPING DEVICE FOR A MEDICAL ACCESS CONNECTOR," the disclosure of which is incorporated herein by reference in its entirety for all purposes.

BACKGROUND

The present technology relates generally to capping. More particularly, the present technology relates to a capping device for a medical access connector.

Medical access connectors are widely used for delivering medical fluid to a patient or for drawing fluid from a patient. Examples of delivered medical fluid include, but are not limited to, medication or intravenous fluid. Examples of fluids that are drawn from a patient include blood and bodily fluids.

A medical access connector can be a needless connector or needle based connector. A medical access connector can be placed, for example, at one end of a catheter while the other end of the catheter is connected to a patient. An actuator or a needle can be inserted into the top of the medical access connector. An actuator can be used with a needless connector whereas a needle can be used with a needle based connector.

BRIEF DESCRIPTION OF THE DRAWINGS

The accompanying drawings, which are incorporated in and form a part of this application, illustrate embodiments of the subject matter, and together with the description of embodiments, serve to explain the principles of the embodiments of the subject matter. The drawings referred to in this description should not be understood as being drawn to scale unless specifically noted.

DETAILED DESCRIPTION

Figure 1:
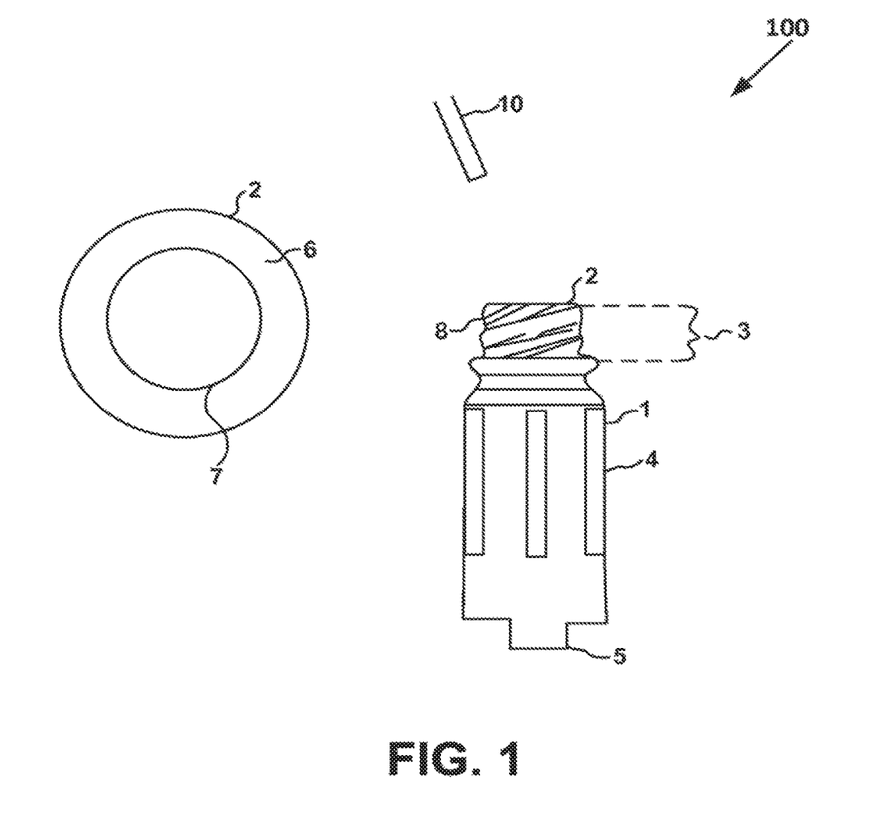
FIG. 1 depicts a conventional medical access connector.

FIG. 1 depicts a conventional medical access connector 100.

The conventional medical access connector 100 has a housing 1 with a top 2, a throat 3, a body 4, and a port 5 located toward the bottom. The top 2 includes a rim 6 of the housing 1 and a valve top 7 where an actuator 10 can be inserted.

According to one embodiment, the medical access connector 100 has male threads 8 around the throat 3. However, according to one embodiment, the threads 8 are not true threads because they do not have any undercuts. Therefore, the threads 8 shall also be referred to as "un-true threads."

A medical access connector 100 can be a needless connector 100 or needle based connector 100. A medical access connector 100 can be placed, for example, at one end of a catheter while the other end of the catheter is connected to a patient. An actuator 10 or a needle can be inserted into the top 2 of the medical access connector 100. An actuator 10 would be used with a needless connector whereas a needle would be used with a need based connector.

The port 5 can be coupled with tubing that connects with a patient's vein. Tubing coupled to the port 5 shall be referred to as "distal tubing." The actuator 10 of a syringe can be inserted into the throat 3 through the valve top 7 to deliver medication to the patient's blood stream or to draw blood. The throat 3 and the syringe may have respective threads 8. For example, the throat 3 may have male threads 8 and the syringe may have female threads that can be used for securely coupling the syringe to the throat 3. Tubing may be connected to the syringe for delivering medication from a source, such as a bottle or bag, of medication. Tubing coupled with the syringe shall be referred to as "proximal tubing."

A user can grasp the conventional medical access connector 100, swab the top 2 of the conventional connector 100, insert the actuator 10 of a syringe through the swabbed connector top 2 to deliver medication, and then release their grasp of the conventional medical access connector 100 after the medication has been delivered.

Figure 2A:
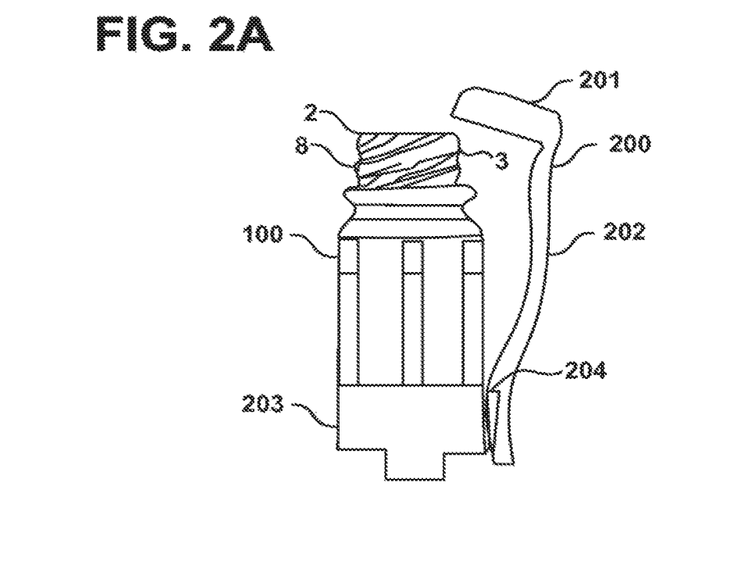
FIGS. 2A and 2B depict diagrams of a medical access connector with a non-symmetrical capping device, according to various embodiments.
Figure 2B:
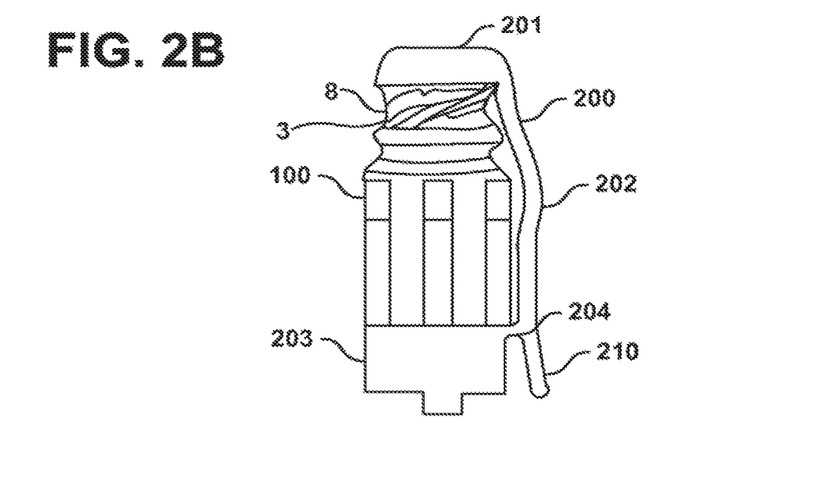

FIGS. 2A and 2B depict diagrams of a medical access connector 100 with a non-symmetrical capping device 200, according to various embodiments. FIG. 2A depicts the medical access connector 100 with a non-symmetrical cap 201 removed, according to one embodiment and FIG. 2B depicts the medical access connector 100 with a non-symmetrical cap 201 applied, according to one embodiment. The capping device 200 may be used with a conventional medical access connector or with a non-conventional medical access connector.

The capping device 200 has a cap 201, a first member 202, a second member 203 and a living hinge 204. The cap 201 is made of one part for covering the entire top 2 of the medical access connector 100. The first member 202 is connected with the cap 201. The second member 203 is connected with the medical access connector 100. According to one embodiment, the cap 201 covers both the valve top 7 (FIG. 1) and the rim 6 (FIG. 1).

The cap 201 is located at one end of the first member 202 and the living hinge 204 is located in the general vicinity of the other end of the first member 202, according to one embodiment. The second member 203, according to one embodiment, wraps around the medical access connector 100. The second member 203 can wrap around the body or the throat, among other things, of the medical access connector 100.

The living hinge 204 is between the first member 202 and the second member 203. The living hinge 204 provides a pivot point between the first member 202 and the second member 203. For example, the first member 202 pivots with respect to the second member 203 at the living hinge 204 as the cap 201 is removed from the medical access connector 100's top 2 in FIG. 2A and then is applied to the medical access connector 100's top 2 as depicted in FIG. 2B.

According to one embodiment, the medical access connector 100 has male threads 8 around the throat 3. However, according to one embodiment, the threads 8 are not true threads 8 (un-true threads) because they do not have any undercuts that would require a cap 201 to be screwed on or screwed off. For example, according to one embodiment, the threads 8 have cuts out of the threads 8, which are not undercuts, which would allow the cap 201 to be pulled free without rotating the cap 201.

According to one embodiment, capping and uncapping of a medical access connector 100 is transparent to a user that is manipulating the medical access connector 100. For example, a user can grasp the medical access connector 100 at location 210 as depicted in FIG. 2B, which automatically causes the cap 201 to be removed as depicted in FIG. 2A, swab the top 2 of the medical access connector 100, insert the actuator 10 (FIG. 1) of a syringe through the swabbed top 2 to deliver medication, and then release their grasp of the medical access connector 100 after the medication has been delivered, which automatically causes the cap 201 to be reapplied to the top 2 as depicted in FIG. 2B.

As can be seen, according to one embodiment, the user's methodology for the conventional medical access connector 100 without a capping device (FIG. 1) and the medical access connector with the capping device 200 is the same. More specifically for both the conventional medical access connector 100 without a capping device (FIG. 1) and the medical access connector with the capping device 200, the user grasped the connectors, inserted the actuator, delivered the medication and then released their grasp. The opening and closing of the cap is automatic, according to various embodiments, when the user grasps and releases their grasp providing a transparent experience for the user. According to one embodiment, the cap 201 is referred to as "self-closing" because it will close automatically when the user releases their grasp of the medical access connector 100.

In contrast, the closing and opening of conventional caps would require the use of two hands and would not be transparent to the user. For example, a user would have to hold a medical access connector with one hand, remove the conventional cap with their other hand and then lay the conventional cap down in order to pick up a syringe.

Further, according to one embodiment, the capping device 200 is configured for manipulation by a single hand. For example, the user is able to grasp the medical access connector 100, open the cap 201 and reapply the cap 201 all with the same hand.

According to one embodiment, the capping device according to various embodiments can be used for any type of medical access connector. For example, the capping device can be used with needless connectors or needle based connectors. Examples of needless connectors include at least split septum and nose split septum.

According to one embodiment, an entire capping device, according to various embodiments, is made from a single molded piece of material. For example, injection molding can be used to create the entire capping device. According to one embodiment, the capping device is made of a softer plastic, such as acrylonitrile butadiene styrene (ABS).

According to one embodiment, a capping device can be sold as a part of a medical access connector or could be manufactured or sold separately, or manufactured and sold separately. The separate capping device can be applied to a medical access connector. A combination of the medical access connector and the capping device may be sold by the company that manufactured it, or sold by a different company than the company that manufactured the combination together.

The manipulation of a cap associated with a capping device, according to various embodiments, is easy, intuitive and user friend. For example, as discussed herein, the cap can be automatically removed when a user grasps a medical access connector at one or more locations and the cap can be automatically closed when the user releases their grasp of the medical access connector. No additional features or devices are used or required to manipulate a cap, according to various embodiments.

Figure 3:
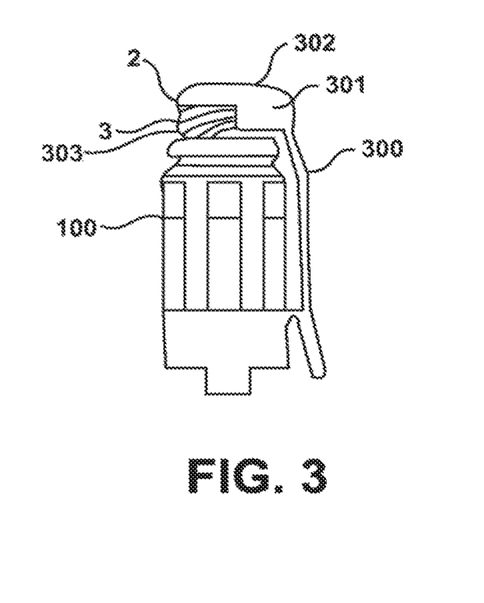
FIG. 3 depicts a non-symmetrical capping device and a medical access connector, according to one embodiment.

FIG. 3 depicts a non-symmetrical capping device 300 and a medical access connector 100, according to one embodiment. As depicted in FIG. 3, a portion 301 of the cap 302 wraps around the sides of the throat 3. A portion 303 of the throat 3 is exposed so that the cap 302 can be removed from the connector 100's top 2.

Figure 4A:
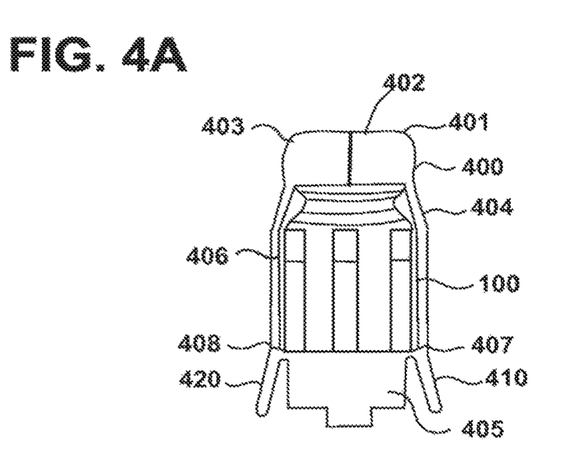
FIGS. 4A-4C depicts a medical access connector with a symmetrical capping device, according to various embodiments.
Figure 4B:
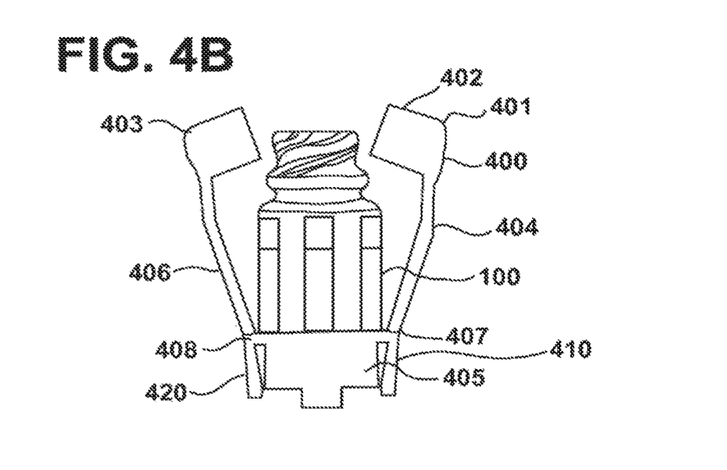
Figure 4C:
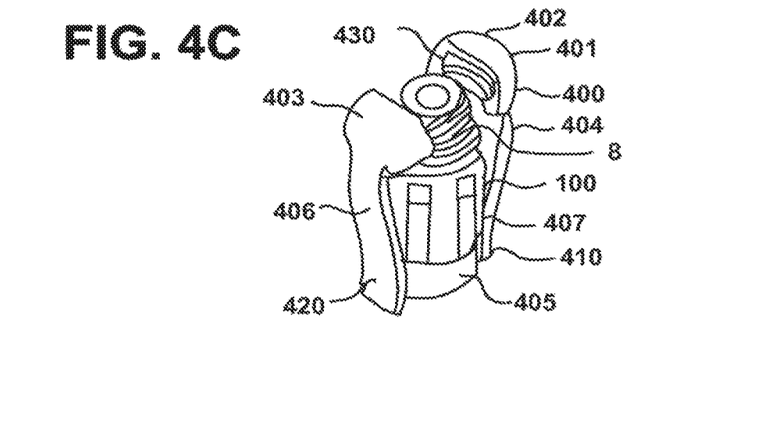

FIGS. 4A-4C depicts a medical access connector 100 with a symmetrical capping device 400, according to one embodiment. FIG. 4A depicts the medical access connector 100 with the cap 401 on. FIGS. 4B and 4C depict the medical access connector 100 with the cap 401 off.

The symmetrical capping device 400 has a cap 401 that has a first cap part 402 and a second cap part 403. The symmetrical capping device 400 has a first member 404 that is connected to the first cap part 402, a second member 405 that is connected with the medical access connector 100, a third member 406 that is connected to the second cap part 403. The symmetrical capping device 400 has a first living hinge 407 and a second living hinge 408. The first living hinge 407 connects the first member 404 and the second member 405. The second living hinge 408 connects the third member 406 and the second member 405. The living hinges 407, 408 provide pivot points between the respective members 404, 405, 406.

The first cap part 402 and the second cap part 403 are located at respective ends of the first member 404 and the third member 406. The living hinges 407, 408 are located in the general vicinity of the other ends of the first member 404 and the third member 406, according to one embodiment. The second member 405, according to one embodiment, wraps around the medical access connector 100. The second member 405 can wrap around the body or the throat, among other things, of the medical access connector 100.

According to one embodiment, the symmetrical capping device 400 can be opened or closed in a manner that is transparent to a user for example by grasping the medical access connector 100 with a single hand at locations 410 and 420. For example, a thumb may be placed at one of the locations 410, 420 and a finger may be placed at the other of the locations 410, 420 when the user grasps the medical access connector 100.

According to one embodiment, the inside 430 of the cap 401 fits, conforms or is a mirror image of the threads 8 of the throat 3. Since the threads 8 are not true threads with undercuts, as discussed herein, the two cap parts 401, 402 will not catch on the threads 8 and, therefore, can be easily pulled away from the throat 3. According to various embodiments, the inside of other types of caps also fit the threads 8 and can be easily pulled away from the throat 3.

Various embodiments are well suited to a two part cap 401 that is divided into half. The sizes of the first cap part and the second cap part may be equal proportions or unequal proportions. For example, the first cap part 402 and the second cap part 403 may be the same size or one of them may be larger than the other.

Figure 5:
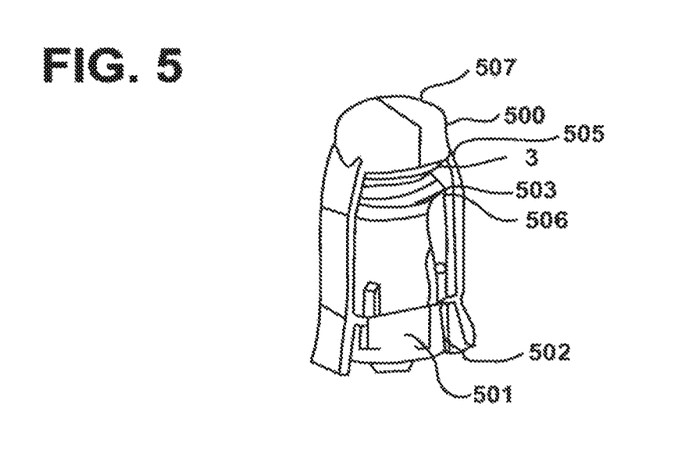
FIG. 5 depicts a capping device that covers most of the surface of a medical access connector, according to one embodiment.

FIG. 5 depicts a capping device 500 that covers most of the surface of a medical access connector, according to one embodiment. For example, as depicted in FIG. 5, the second member 501 extends from the bottom 502 of the housing to a lower edge 503 of the throat 3. As depicted, the upper edge 506 of the second member 501 is not flush with the lower edge 505 of the cap 507. The upper edge 506 of the second member 501 may be flush with the lower edge 505 of the cap 507, according to one embodiment.

Various embodiments are well suited for different types of caps. For example, FIGS. 2A, 2B and 3 depict capping devices with caps that are made of one part. FIGS. 4A-5 depict capping devices with caps that are made of two parts.

FIGS. 6A-6H depict various types of caps for capping devices, according to various embodiments.

Figure 6A:
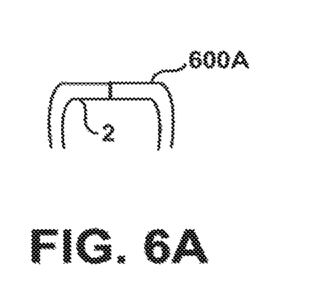
FIGS. 6A-6H depict various types of caps for capping devices, according to various embodiments.
Figure 6B:
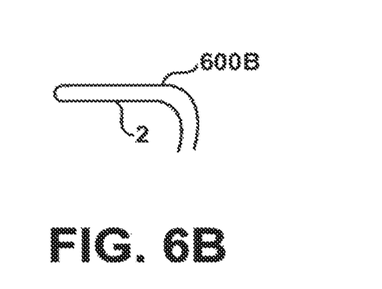

According to one embodiment, the cap is flush with the top of the medical access connector when it is closed. FIG. 6A depicts a cross section of a cap 600A with two parts that is flush with the top 2 of the housing, according to one embodiment. FIG. 6B depicts a cross section of a cap 600B made of one part that is flush with the top 2 of the housing, according to one embodiment.

Figure 6C:
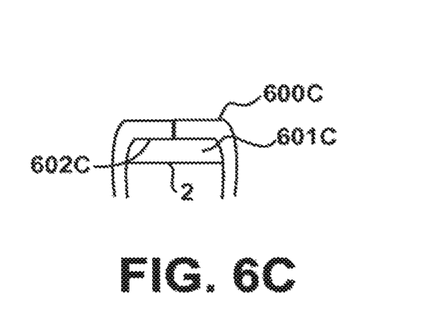
Figure 6D:
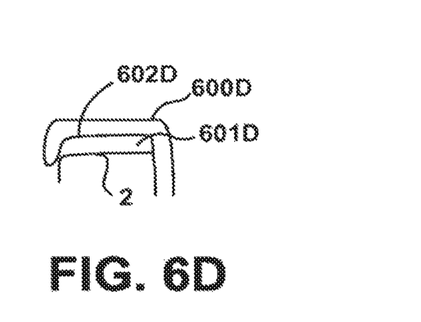

FIG. 6C depicts a cross section of a cap 600C with two parts that is not flush with the top 2 of the housing, according to one embodiment. FIG. 6D depicts a cross section of a cap 600D made of one part that is not flush with the top 2 of the housing, according to one embodiment. As depicted in FIGS. 6C and 6D, there is a gap 601C, 601D between the lower surface 602C, 602D of the cap 600C, 600D and the top 2 of the housing.

Figure 6E:
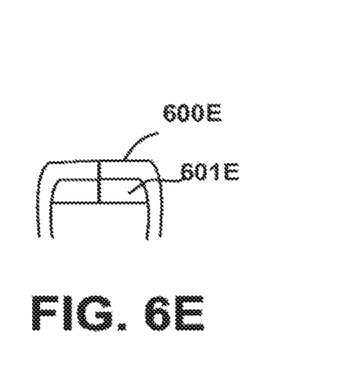
Figure 6F:
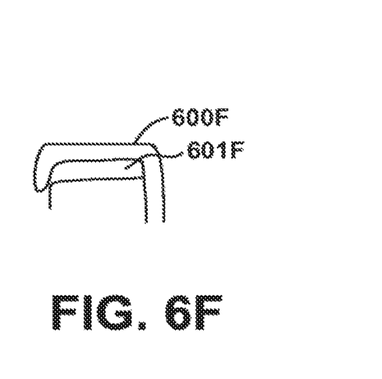
Figure 6G:
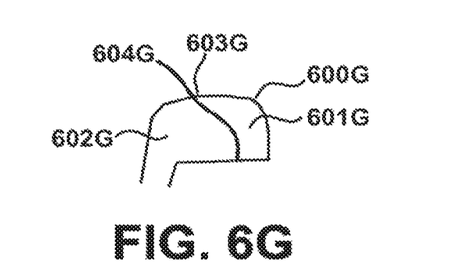

According to one embodiment, a cap can include a microbial membrane that can be used, for example, to swab the top of the housing. FIG. 6E depicts a cross section of a cap 600E with two parts that has a microbial membrane 601E, according to one embodiment. A first part of the microbial membrane is coupled with the first cap part and a second part of the microbial membrane is coupled with the second cap part. FIG. 6G depicts a cross section of a cap 600F made of one part that has a microbial membrane 601F, according to one embodiment. A microbial membrane 601E, 601F may be impregnated with an antimicrobial. The microbial membrane 601E, 601F may be alcohol or some other type of antimicrobial. The microbial membrane 601E, 601F may be made of a compressible material.

Figure 6H:
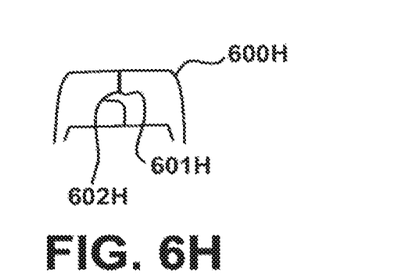

Two parts of a cap may be coupled with each other using, for example, some type of fastener or may rest flush against each other without the use of a fastener. FIG. 6G depicts a two part cap 600G where the two parts 601G, 602G that rest flush against each other at their respective edges 603G, 604G, according to one embodiment. In this example, no fastener is used to couple the two cap parts 601G, 602G together. For example, the force exerted by the respective living hinges associated with the respective two cap parts 601G, 602G may be sufficient to cause the edges 603G, 604G of respective cap parts 601G, 602G to remain flush against each other. FIG. 6H depicts a side view of a two part cap 600H that are fastened together, according to one embodiment. For example, a male portion 601H of the fastener associated with the first cap part is positioned inside of a female portion 602H associated with the second cap part. Various embodiments are well suited for other types of fasteners.

Various embodiments are well suited for capping devices with various dimensions. For example, various embodiments are well suited for capping devices with varying heights, widths, thicknesses. For example, the capping device may be shorter or longer or a part, such as the cap, or a first, second, or third member may be shorter or longer. In another example, the width of the capping device may be wider or narrower, for example, to be compatible with medical access connectors that are wider or narrower. The thickness of a part may vary. For example, the cap, a first member, a second member, or one or more living hinges, among others, may be thicker or thinner. One or more living hinges may be shorter or longer.

Further, various embodiments are well suited for capping devices that cover all of the threads of the throat or that do not cover all of the threads of the throat. FIGS. 4A, 4B, 4C and 5 depict capping devices that cover all of the threads of the throat. FIGS. 2A and 2B depict capping devices that do not cover all of the threads of the throat.

Figure 7:
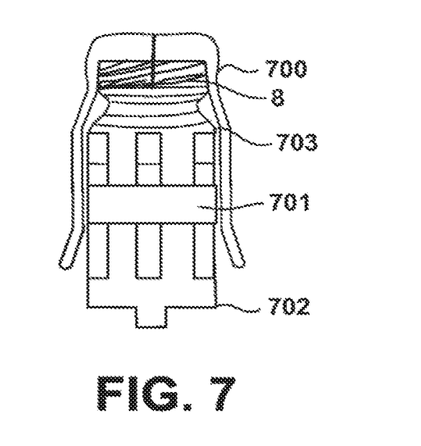
FIG. 7 depicts another capping device where there are exposed threads because the cap does not cover all of the threads of the throat, according to one embodiment.

FIG. 7 depicts another capping device 700 where some of the threads 8 are exposed because the cap does not cover all of the threads 8 of the throat, according to one embodiment. Further, the second member 701 depicted in FIG. 7 does not extend all the way to the bottom 702 of the medical access connector 100, according to one embodiment. Although FIG. 7 is depicted with a symmetrical capping device 700, various embodiments are well suited for a nonsymmetrical capping device where the cap does not cover all of the threads 8 of the throat. Although FIG. 7 is depicted with a second member 701 that does not extend to the bottom 602 of the medical access connector 100, various embodiments are well suited for a second member that extends to the bottom 702, or to the lower edge of the throat 703, or a combination thereof.

Figure 8:
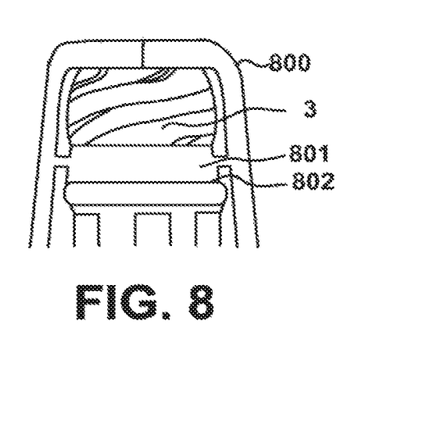
FIG. 8 depicts a capping device that substantially resides on the throat of a medical access connector, according to one embodiment.

FIG. 8 depicts a capping device 800 that substantially resides on the throat 3 of a medical access connector, according to one embodiment. For example, the second member 801 is located on the throat 3. Although FIG. 8 is depicted with a symmetrical capping device 800, various embodiments are well suited for a non-symmetrical capping device that substantially resides on the throat 3 of a medical access connector. Although FIG. 8 depicts a capping device 800 where the second member 801 is positioned toward the bottom 802 of the throat 3, various embodiments are well suited for a second member 801 that is positioned with some of the threads 8 of the throat 3 that are above the second member 801 and some of the treads 8 are below the second member 801.

Figure 9:
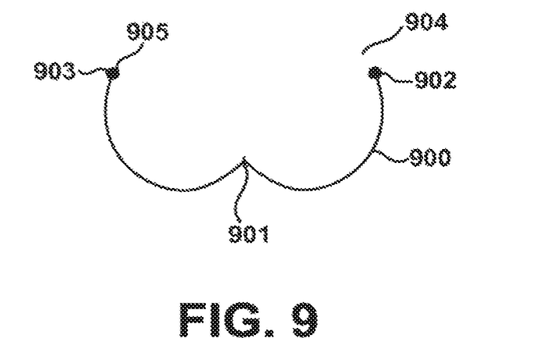
FIG. 9 depicts a top down view of a second member, according to one embodiment, that can be used for coupling a separate capping device with a medical access connector.

According to various embodiments, capping devices as depicted in FIGS. 2A-8 may be manufactured separately or sold separately, or a combination thereof from medical access connectors. FIG. 9 depicts a top down view of a second member 900, according to one embodiment, that can be used for coupling a separate capping device with a medical access connector. The second member 900 can include a hinge 901. The hinge 901 may be a living hinge. The second member 900 may include a fastener for fastening the two open ends 902, 903 of the second member 900 where one part 904 of the fastener is associated with the first open end 902 and the other part 905 of the fastener is associated with the second open end 309 of the fastener.

According to one embodiment, a capping device can be coupled with a medical access connector, for example, by sliding the capping device onto the medical access connector.

According to one embodiment, the capping device according to various embodiments can be used for any type of medical access connector. For example, the capping device can be used with needless connectors or needle based connectors. Examples of needless connectors include at least split septum and nose split septum.

According to one embodiment, an entire capping device, according to various embodiments, is made from a single molded piece of material. For example, injection molding can be used to create the entire capping device. According to one embodiment, the capping device is made of a softer plastic, such as acrylonitrile butadiene styrene (ABS).

The second member of either a symmetrical capping device or a nonsymmetrical capping device can be located on the threads or the body or partially on the threads or partially on the body.

According to one embodiment, a capping device can be sold as a part of a medical access connector or could be manufactured or sold separately, or manufactured and sold separately. The separate capping device can be applied to a medical access connector. A combination of a capping device and medical access connector may be sold by the company that manufactured it, or may be sold by a different company than the company that manufactured it.

The manipulation of a cap associated with a capping device, according to various embodiments, is easy, intuitive and user friend. For example, as discussed herein, the cap can be automatically removed when a user grasps a medical access connector at one or more locations and the cap can be automatically closed when the user releases the medical access connector. No additional features or devices are used or required to manipulate a cap, according to various embodiments.

Application and removal of conventional caps would require the use of two hands and would not be transparent to the user. For example, a user would have to hold a medical access connector with one hand, remove the conventional cap with their other hand and then lay the conventional cap down in order to pick up a syringe. The conventional cap may fall or get lost.

Various embodiments of a capping device are not obvious for many reasons. For example, the incursion of microbes from connectors can occur especially in the case of connectors with a split septum or from around the perimeter or rim of the connector. The incursion of microbes into the blood stream can lead to serious illnesses and even death. Therefore, there as been a long felt need for a capping device, according to various embodiments, that reduces the probability of infection.

However, there has been a failure by others to recognize the problem. For example, designers have believed that the problems of preventing the incursion of microbes or other contaminates into the blood stream from a medical access connector had already been sufficiently addressed by providing smooth swab able easy to clean surfaces, such as the top or sides, or a combination thereof, on the conventional medical access connectors.

Further, there has been a failure of others to determine a solution. For example, designers have believed that the removal and application of a cap would require the use of two hands and that the cap can be dropped or lost. In some circumstances, the user may need to use one hand to hold a vein to keep blood from leaking and to use the other hand to manipulate the connector. In this case, there would be no additional hands to manipulate a cap.

Therefore, a capping device for a medical access connector that can be capped or uncapped transparently to the user that is manipulating the medical access connector or medical container or that is configured for manipulation by a single hand is not obvious.

Various embodiments are also well suited for using a capping device with a medical container such as a bag or bottle containing medical fluid, such as medication or intravenous fluid, among other things.

The features depicted in FIGS. 2A-9 can be arranged differently than as illustrated, and can implement additional or fewer features than what are described herein. Further, the features depicted in FIGS. 2A-9 can be combined in various ways.

Example embodiments of the subject matter are thus described. Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

Various embodiments have been described in various combinations and illustrations. However, any two or more embodiments or features may be combined. Further, any embodiment or feature may be used separately from any other embodiment or feature. Phrases, such as "an embodiment," "one embodiment," among others, used herein, are not necessarily referring to the same embodiment. Features, structures, or characteristics of any embodiment may be combined in any suitable manner with one or more other features, structures, or characteristics.

What is claimed is:

1. A capping device for a medical access connector comprising:
    a first cap and a second cap, the first and second caps having first and second inside surfaces, respectively, for covering a top of the medical access connector when the capping device is in a closed configuration where the first and second caps are engaged against each other;
    a first member extending between the first cap and a second member configured to couple with the medical access connector, wherein a first living hinge is formed between the first and second members; and
    a third member extending between the second cap and the second member, wherein a second living hinge is formed between the third and second members;
    wherein, in the closed configuration, the first and second inside surfaces are spaced from the top of the medical access connector by a gap, and
    wherein a male fastener portion of the first cap is configured to fasten with a female fastener portion of the second cap in the closed configuration.

2. The capping device for a medical access connector of claim 1, wherein the first cap comprises a first engagement face configured to engage against a second engagement face of the second cap, and wherein a force exerted by the first and second living hinges cause the first and second engagement faces to rest flush against each other in the closed configuration.

3. The capping device for a medical access connector of claim 1, wherein any of the first and second inside surfaces comprises a microbial membrane configured to engage against the top of the medical access connector in the closed configuration.

4. The capping device for a medical access connector of claim 3, wherein the microbial membrane is made of a compressible material.

5. The capping device for a medical access connector of claim 1, wherein each of the first and second caps comprises an outer surface size having unequal proportions relative to each other.

6. The capping device for a medical access connector of claim 1, wherein each of the first and second caps comprises an outer surface size having equal proportions relative to each other.

7. A medical access connector system comprising:
a medical access connector having a housing comprising a top with a rim extending around a valve top;
a capping device having:
  a first cap and a second cap, the first and second caps having first and second inside surfaces, respectively, for covering the top of the housing when the capping device is in a closed configuration where the first and second caps are engaged against each other;
  a first member extending between the first cap and a second member coupled with the housing, wherein a first living hinge is formed between the first and second members; and
  a third member extending between the second cap and the second member, wherein a second living hinge is formed between the third and second members,
wherein, in the closed configuration, the first and second inside surfaces are spaced from the top of the housing by a gap, and
wherein a first fastener portion of the first cap is configured to fasten with a second fastener portion of the second cap in the closed configuration.

8. The medical access connector system of claim 7, wherein the top of the housing comprises the rim extending around the valve top, and the first and second caps cover the rim and valve top in the closed configuration.

9. The medical access connector system of claim 7, wherein the first cap comprises a first engagement face configured to engage against a second engagement face of the second cap, and wherein a force exerted by the first and second living hinges cause the first and second engagement faces to rest flush against each other in the closed configuration.

10. The medical access connector system of claim 7, wherein a portion of the housing, adjacent the top, comprises a throat having an outer surface comprising a thread.

11. The medical access connector system of claim 7, wherein the second member extends around an outer surface of the housing, between the first and third members.

12. The medical access connector system of claim 7, wherein a portion of the housing, adjacent the top, comprises a throat, and wherein the second member extends around the throat.

13. The medical access connector system of claim 7, wherein any of the first and second inside surfaces comprises a microbial membrane configured to engage against the top of the housing in the closed configuration.

14. The medical access connector system of claim 7, wherein the housing comprises an outer surface having a thread, and any of the first and second inside surfaces comprises reciprocal threads configured to engage the thread of the housing in the closed configuration.

* * * * *